(12) United States Patent
Kiani et al.

(10) Patent No.: US 11,839,470 B2
(45) Date of Patent: *Dec. 12, 2023

(54) ACTIVE-PULSE BLOOD ANALYSIS SYSTEM

(71) Applicant: Masimo Corporation, Irvine, CA (US)

(72) Inventors: Massi Joe E. Kiani, Laguna Niguel, CA (US); Mathew Paul, Irvine, CA (US); Jesse Chen, Foothill Ranch, CA (US); Marcelo M. Lamego, Cupertino, CA (US)

(73) Assignee: MASIMO CORPORATION, Irvine, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 17/576,281

(22) Filed: Jan. 14, 2022

(65) Prior Publication Data

US 2022/0133189 A1    May 5, 2022

Related U.S. Application Data

(63) Continuation of application No. 16/804,507, filed on Feb. 28, 2020, now Pat. No. 11,224,363, which is a continuation of application No. 15/670,405, filed on Aug. 7, 2017, now Pat. No. 10,610,139, which is a continuation of application No. 14/328,694, filed on Jul. 10, 2014, now Pat. No. 9,724,025, which is a continuation-in-part of application No. 14/153,393, filed on Jan. 13, 2014, now abandoned.

(60) Provisional application No. 61/844,699, filed on Jul. 10, 2013, provisional application No. 61/752,976, filed on Jan. 16, 2013.

(51) Int. Cl.
*A61B 5/1455* (2006.01)
*A61B 5/00* (2006.01)

(52) U.S. Cl.
CPC ........ *A61B 5/14552* (2013.01); *A61B 5/6826* (2013.01); *A61B 5/721* (2013.01); *A61B 5/7207* (2013.01)

(58) Field of Classification Search
CPC . A61B 5/14552; A61B 5/6826; A61B 5/7207; A61B 5/721
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Hink et al. | |

(Continued)

*Primary Examiner* — Eric F Winakur
(74) *Attorney, Agent, or Firm* — Knobbe Martens, Olson & Bear LLP

(57) ABSTRACT

An active-pulse blood analysis system has an optical sensor that illuminates a tissue site with multiple wavelengths of optical radiation and outputs sensor signals responsive to the optical radiation after attenuation by pulsatile blood flow within the tissue site. A monitor communicates with the sensor signals and is responsive to arterial pulses within a first bandwidth and active pulses within a second bandwidth so as to generate arterial pulse ratios and active pulse ratios according to the wavelengths. An arterial calibration curve relates the arterial pulse ratios to a first arterial oxygen saturation value and an active pulse calibration curve relates the active pulse ratios to a second arterial oxygen saturation value. Decision logic outputs one of the first and second arterial oxygen saturation values based upon perfusion and signal quality.

17 Claims, 13 Drawing Sheets

(56) References Cited

U.S. PATENT DOCUMENTS

| | | |
|---|---|---|
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,754 A | 7/1998 | Korf et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |

(56) References Cited

U.S. PATENT DOCUMENTS

| | | |
|---|---|---|
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |

(56) References Cited

U.S. PATENT DOCUMENTS

| | | | |
|---|---|---|---|
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |

(56) References Cited

U.S. PATENT DOCUMENTS

| | | |
|---|---|---|
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |

(56) References Cited

U.S. PATENT DOCUMENTS

| | | |
|---|---|---|
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Ai-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Ai-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |

(56) References Cited

U.S. PATENT DOCUMENTS

| | | |
|---|---|---|
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| 11,224,363 B2 | 1/2022 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| 11,678,829 B2 | 6/2023 | Al-Ali et al. |
| 11,692,934 B2 | 7/2023 | Normand et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0211925 A1 | 9/2006 | Lamego et al. |
| 2006/0238358 A1 | 10/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2010/0274099 A1 | 10/2010 | Telfort et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |

(56) References Cited

U.S. PATENT DOCUMENTS

| | | |
|---|---|---|
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081100 A1 | 3/2014 | Muhsin et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2015/0380875 A1 | 12/2015 | Coverston et al. |
| 2016/0029932 A1 | 2/2016 | Al-Ali |
| 2016/0051205 A1 | 2/2016 | Al-Ali et al. |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0103874 A1 | 4/2018 | Lee et al. |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |

(56) References Cited

U.S. PATENT DOCUMENTS

| | | |
|---|---|---|
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |

ACTIVE-PULSE BLOOD ANALYSIS SYSTEM

The present application is a continuation of U.S. patent application Ser. No. 16/804,507, filed Feb. 28, 2020, which is a continuation of U.S. patent application Ser. No. 15/670,405, filed Aug. 7, 2017, which is a continuation of U.S. patent application Ser. No. 14/328,694, which is a continuation-in-part of U.S. patent application Ser. No. 14/153,393, filed Jan. 13, 2014, titled Active-Pulse Blood Analysis System, which claims priority benefit under 35 U.S.C. § 119(e) to U.S. Provisional Patent Application Ser. No. 61/752,976, filed Jan. 16, 2013, titled Active-Pulse Blood Analysis System; the U.S. patent application Ser. No. 14/328,694 claims priority benefit under 35 U.S.C. § 119(e) to U.S. Provisional Patent Application Ser. No. 61/844,699, filed Jul. 10, 2013, titled Active-Pulse Blood Analysis System; all of the above-referenced patent applications and provisional patent applications are hereby incorporated in their entireties by reference herein.

PRIORITY CLAIM AND REFERENCE TO RELATED APPLICATIONS

The present application is a continuation-in-part of U.S. patent application Ser. No. 14/153,393, filed Jan. 13, 2014, titled Active-Pulse Blood Analysis System, which claims priority benefit under 35 U.S.C. § 119(e) to U.S. Provisional Patent Application Ser. No. 61/752,976, filed Jan. 16, 2013, titled Active-Pulse Blood Analysis System; the present application claims priority benefit under 35 U.S.C. § 119(e) to U.S. Provisional Patent Application Ser. No. 61/844,699, filed Jul. 10, 2013, titled Active-Pulse Blood Analysis System; the above-referenced patent application and provisional patent applications are hereby incorporated in their entireties by reference herein.

BACKGROUND OF THE INVENTION

Noninvasive physiological monitoring systems for measuring constituents of circulating blood have advanced from basic pulse oximeters to monitors capable of measuring abnormal and total hemoglobin among other parameters. A basic pulse oximeter capable of measuring blood oxygen saturation typically includes an optical sensor, a monitor for processing sensor signals and displaying results and a cable electrically interconnecting the sensor and the monitor. A pulse oximetry sensor typically has a red wavelength light emitting diode (LED), an infrared (IR) wavelength LED and a photodiode detector. The LEDs and detector are attached to a patient tissue site, such as a finger. The cable transmits drive signals from the monitor to the LEDs, and the LEDs respond to the drive signals to transmit light into the tissue site. The detector generates a photoplethysmograph signal responsive to the emitted light after attenuation by pulsatile blood flow within the tissue site. The cable transmits the detector signal to the monitor, which processes the signal to provide a numerical readout of oxygen saturation ($SpO_2$) and pulse rate, along with an audible pulse indication of the person's pulse. The photoplethysmograph waveform may also be displayed.

SUMMARY OF THE INVENTION

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, California and are incorporated in their entireties by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated in their entireties by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad8®, Rad5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, California ("Cercacor") and all incorporated in their entireties by reference herein. An advanced parameter measurement system that includes acoustic monitoring is described in U.S. Pat. Pub. No. 2010/0274099, filed Dec. 21, 2009, titled Acoustic Sensor Assembly, assigned to Masimo and incorporated in its entirety by reference herein.

Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad87™ and Rad57™ monitors, all available from Masimo. Advanced parameter measurement systems may also include acoustic monitoring such as acoustic respiration rate (RRa™) using a Rainbow Acoustic Sensor™ and Rad87™ monitor, available from Masimo. Such advanced pulse oximeters, low noise sensors and advanced parameter systems have gained rapid acceptance in a wide variety of medical applications, including surgical wards, intensive care and neonatal units, general wards, home care, physical training, and virtually all types of monitoring scenarios.

One aspect of an active-pulse blood analysis system has an optical sensor that illuminates a tissue site with multiple wavelengths of optical radiation and that outputs sensor signals responsive to the optical radiation after attenuation by pulsatile blood flow within the tissue site. A monitor communicates with the sensor signals and is responsive to arterial pulses within a first bandwidth and active pulses within a second bandwidth so as to generate arterial pulse ratios and active pulse ratios according to the wavelengths. An arterial calibration curve relates the arterial pulse ratios to a first arterial oxygen saturation, and a first active pulse calibration curve relates the active pulse ratios to a first venous oxygen saturation.

In various embodiments, the arterial calibration curve relates the active pulse ratios to a second venous oxygen saturation. A second active pulse calibration curve relates the active pulse ratios to a second arterial oxygen saturation. A multiplexer selects from the first arterial oxygen saturation and the second arterial oxygen saturation so as to output a third arterial oxygen saturation. A decision logic determines the third arterial oxygen saturation. The decision logic receives a motion input and a perfusion input. The decision logic selects the third arterial oxygen saturation when perfusion is in a lower range of perfusion values and motion is in a higher range of motion values.

Another aspect of an active-pulse blood analysis system inputs optical sensor data, filters the sensor data into arterial pulse data at a lower range of frequencies and active pulse data at a higher range of frequencies, calculates arterial pulse ratios from the arterial pulse data and active pulse ratios from the active pulse data, applies an arterial calibration curve to the arterial pulse ratios so as to generate an $SpO_2$ parameter and applies a second calibration curve so as to generate a second oxygen saturation parameter. In various embodiments, the second calibration curve is a venous calibration curve and the second oxygen saturation parameter is $SpvO_2$, the second calibration curve is an arterial calibration curve and the second oxygen saturation parameter is $SpvO_2^A$, the second calibration curve relates active pulse ratio data to $SaO_2$ values so as to define an arterial saturation parameter $SpO_2^{AP}$.

In various other embodiments, one of the $SpO_2$ parameter and the $SpO_2^{AP}$ are output according to a motion and perfusion selection criterion. The selection criterion is based upon motion zones and perfusion zones. The selection criterion is based upon a boundary between a first area of relatively high perfusion combined with relatively little motion and a second area of relatively low perfusion combined with relatively large motion.

A further aspect of an active-pulse blood analysis system is an optical sensor for transmitting multiple wavelengths of light into a tissue site and detecting the transmitted light after attenuation by arterial blood flow and active pulse blood flow within the tissue site so as to generate plethysmograph data. A filter separates the detected plethysmograph data into arterial pulse data and active pulse data. A processor calculates arterial ratios from the arterial pulse data and active pulse ratios from the active pulse data. An arterial calibration curve relates the arterial pulse ratios to $SpO_2$ values, and a venous calibration curve relates the active pulse ratios to $SpvO_2$ values. In various embodiments, an arterial cal curve relates the active pulse ratios to $SpvO_2^A$ values, an active pulse cal curve relates the active pulse ratios to $SpO_2^{AP}$ values, a multiplexor relates $SpO_2$ and $SpO_2^{AP}$ values to $SpO_2^M$ values, a decision logic selects $SpO_2$ and $SpO_2^{AP}$ to output as $SpO_2^M$ according to a combination of motion and perfusion, and a zone specifies the decision logic according to motion and perfusion.

Yet another aspect of an active-pulse blood analysis system is an optical sensor that illuminates a tissue site with multiple wavelengths of optical radiation and that outputs sensor signals responsive to the optical radiation after attenuation by pulsatile blood flow within the tissue site. A monitor communicates with the sensor signals and is responsive to arterial pulses within a first bandwidth and active pulses within a second bandwidth so as to generate arterial pulse ratios and active pulse ratios according to the wavelengths. An arterial calibration curve relates the arterial pulse ratios to a first arterial oxygen saturation ($SpO_2$), and an active pulse calibration curve relates the active pulse ratios to a second arterial oxygen saturation ($SpO_2^{AP}$).

In various embodiments, a multiplexer has a third arterial oxygen saturation ($SpO_2^M$) output selected from one of the first arterial oxygen saturation and the second arterial oxygen saturation. A decision logic determines the third arterial oxygen saturation. Signal quality and perfusion are input to the decision logic. The decision logic selects the second arterial oxygen saturation when perfusion is in a lower range of perfusion values and signal quality is in a lower range of signal quality values. The decision logic inputs a Boolean perfusion value (BPI) and a Boolean signal quality value (BSQ).

An additional aspect of an active-pulse blood analysis system is inputting optical sensor data, filtering the optical sensor data into arterial pulse data at a lower range of frequencies and active pulse data at a higher range of frequencies, calculating arterial pulse ratios from the arterial pulse data. Active pulse ratios are calculated from the active pulse data. An arterial calibration curve is applied to the arterial pulse ratios so as to generate an $SpO_2$ parameter indicative of arterial oxygen saturation determined from an arterial pulse. An active pulse calibration curve is applied to the active pulse ratios so as to generate an $SpO_2^{AP}$ parameter indicative of arterial oxygen saturation determined from an active pulse.

In various embodiments, active-pulse blood analysis comprises multiplexing the $SpO_2$ parameter and the $SpO_2^{AP}$ parameter so as to generate an $SpO_2^M$ output parameter indicative of an arterial oxygen saturation measurement tolerate to at least one of motion, low perfusion and low signal quality. Multiplexing comprises selecting one of the $SpO_2$ parameter and the $SpO_2^{AP}$ parameter as the $SpO_2^M$ output parameter according to a combination of a signal quality input and a perfusion index input. Selecting comprises outputting $SpO_2^{AP}$ as the $SpO_2^M$ output parameter when the combination of signal quality and perfusion are below a threshold boundary. Selecting comprises outputting $SpO_2$ as the $SpO_2^M$ output parameter when the combination of signal quality and perfusion are above the threshold boundary. The threshold boundary is specified by discrete zones of signal quality and perfusion. The threshold boundary is specified by a continuous curve that is a function of signal quality and perfusion.

Further aspects of an active-pulse blood analysis apparatus comprise an optical sensor means for transmitting multiple wavelengths of light into a tissue site and detecting the transmitted light after attenuation by arterial blood flow and active pulsed blood flow within the tissue site so as to generate plethysmograph data. A filter means separates the detected plethysmograph data into arterial pulse data and active pulse data. A processor means calculates arterial ratios from the arterial pulse data and active pulse ratios from the active pulse data. An arterial calibration curve means relates the arterial pulse ratios to oxygen saturation values ($SpO_2$). An active pulse calibration curve means relates the active pulse ratios to active pulse oxygen saturation values ($SpO_2^{AP}$).

In various embodiments, the active-pulse blood analysis apparatus a further comprising a multiplexer means for combining the oxygen saturation values and active pulse oxygen saturation values into multiplexed oxygen saturation values ($SpO_2^M$). A decision logic means selects from $SpO_2$ and $SpO_2^{AP}$ as the $SpO_2^M$ output. The decision logic means is responsive to at least two of motion, perfusion and signal quality inputs.

BRIEF DESCRIPTION OF THE DRAWINGS

FIG. 2A illustrates a prior art occlusive, off-site active-pulse technique for temporally-spaced (non-concurrent) arterial and venous oxygen saturation measurements;

FIG. 2B illustrates a non-occlusive, on-site active-pulse technique for concurrent $SpO_2$ and $SpvO_2$ measurements;

FIG. 6A is a graph of two-dimensional $SpO_2$ and $SpvO_2$ cal curves;

FIG. 6B is a graph of a multi-dimensional $SpvO_2$ cal curve;

FIG. 8A is a graph of an arterial cal curve for calculating $SpO_2$; and

FIG. 8B is a graph of an identical arterial cal curve for calculating $SpvO_2^A$;

FIG. 10A is a two-dimensional $SpO_2^{AP}$ cal curve shown in relation to a $SpO_2$ cal curve; and FIG. 10B is a multidimensional $SpO_2^{AP}$ cal curve;

DETAILED DESCRIPTION OF THE PREFERRED EMBODIMENTS

Figure 1:
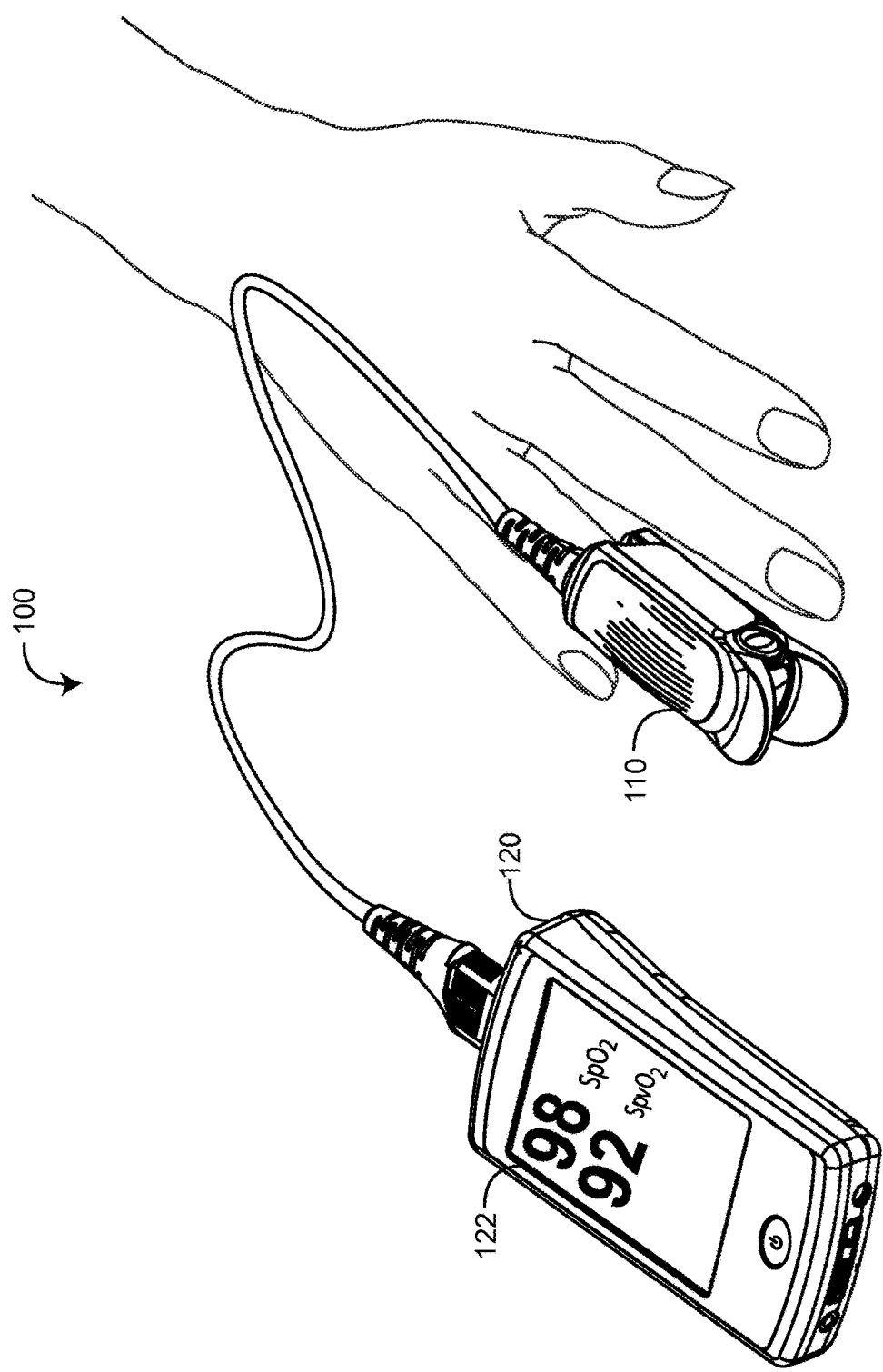
FIG. 1 is an illustration of an active-pulse blood analysis system for concurrently determining a person's arterial oxygen saturation ($SpO_2$) and venous oxygen saturation ($SpvO_2$)

FIG. 1 illustrates an active-pulse blood analysis system 100 for concurrently determining a person's arterial oxygen saturation ($SpO_2$) and venous oxygen saturation ($SpvO_2$). The active-pulse blood analysis system 100 has an optical sensor 110 that transmits optical radiation at two or more wavelengths including red and infrared wavelengths. The active-pulse blood analysis system 100 also has a monitor 120 that determines the relative concentrations of blood constituents flowing in optically-probed pulsatile arteries and actively-pulsed capillaries and veins. A monitor display 122 is configured to readout concurrently measured oxygen saturation values including $SpO_2$, $SpvO_2$, $SpvO_2^A$, $SpO_2^{AP}$ and $SpO_2^M$, as described below. A non-invasive blood analysis system utilizing an optical, active-pulse sensor is described in U.S. patent application Ser. No. 13/646,659 titled Noninvasive Blood Analysis System, filed Oct. 5, 2012, assigned to Cercacor and incorporated in its entirety by reference herein.

Figure 2B:
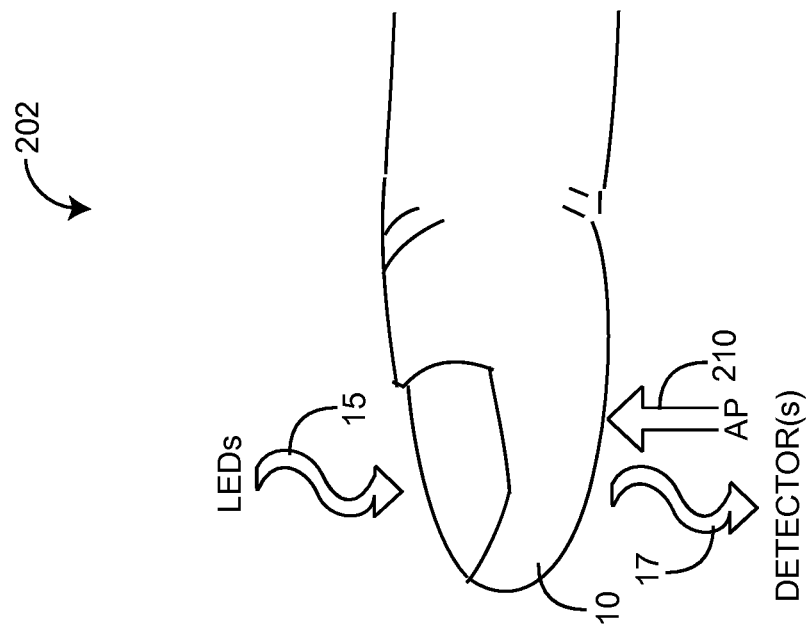
FIGS. 2A-B are illustrations of active-pulse blood analysis techniques.
Figure 2A:
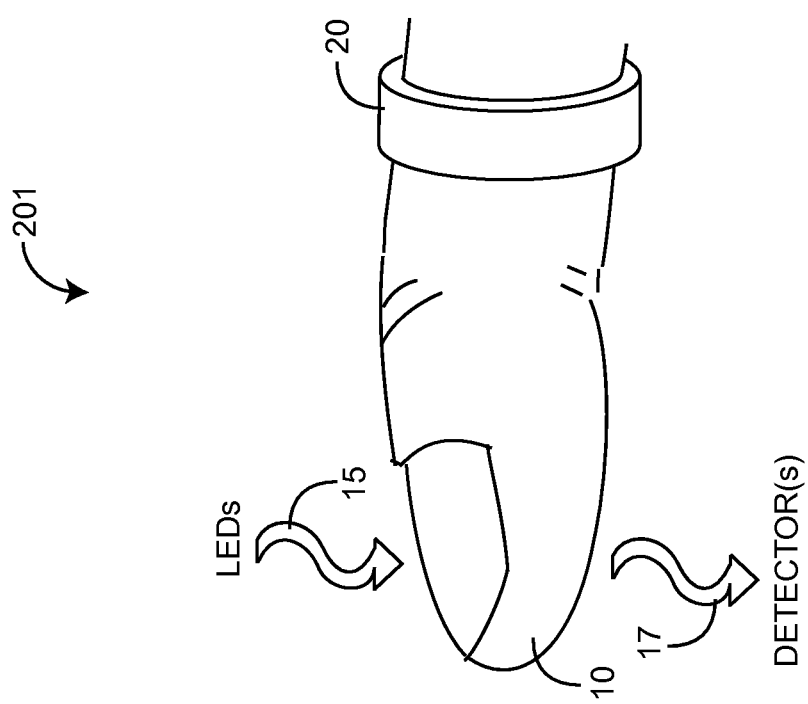

FIGS. 2A-B illustrate active-pulse blood analysis techniques. FIG. 2A illustrates a prior art occlusive, off-site active-pulse technique for temporally-spaced (non-concurrent) arterial and venous oxygen saturation measurements. A fingertip 10 is illuminated 15 with multiple wavelength light from, say, red and IR LEDs. Corresponding multiple wavelength light 17 emerges from the fingertip 10 after attenuation by pulsatile blood flow within the fingertip 10 and is received by detectors accordingly. The artificial pulse mechanism is a pressure cuff 20, as shown, or a plunger or similar mechanical device located distal the fingertip 10. An active-pulse sensor utilizing an off-site plunger or pressure cuff is described in U.S. Pat. No. 6,334,065, titled Stereo Pulse Oximeter, filed May 27, 1999, assigned to Masimo and incorporated in its entirety by reference herein. The downside to such an off-site active-pulse technique is that at least partial occlusion of the arterial blood flow occurs. As a result, accurate optical measurement of arterial blood constituents cannot be made concurrently with venous blood constituents. However, on-site active-pulse techniques present the difficulty of designing a mechanism that generates a pulse co-located with detectors, where the detected light tends to be sensitive to fingertip placement, vibration and movement. Further, conventional wisdom is that an on-site active (artificial) pulse alters or interferes with an arterial pulse such that concurrent measurement of arterial and venous blood constituents is infeasible.

FIG. 2B illustrates a non-occlusive, on-site active-pulse technique for concurrent $SpO_2$ and $SpvO_2$ measurements. In particular, a mechanical pulser 210 is co-located with sensor detectors at the fingertip 10 so that LED light 15 can be detected 17 after attenuation by pulsatile arterial, capillary and venous blood flow. An active-pulse optical sensor having mechanical, optical and electrical elements configured for concurrent probing of arterial, capillary and venous blood constituents is described in U.S. patent application Ser. No. 13/473,377, titled Personal Health Device, filed May 16, 2012, assigned to Cercacor and incorporated in its entirety by reference herein.

Figure 3:
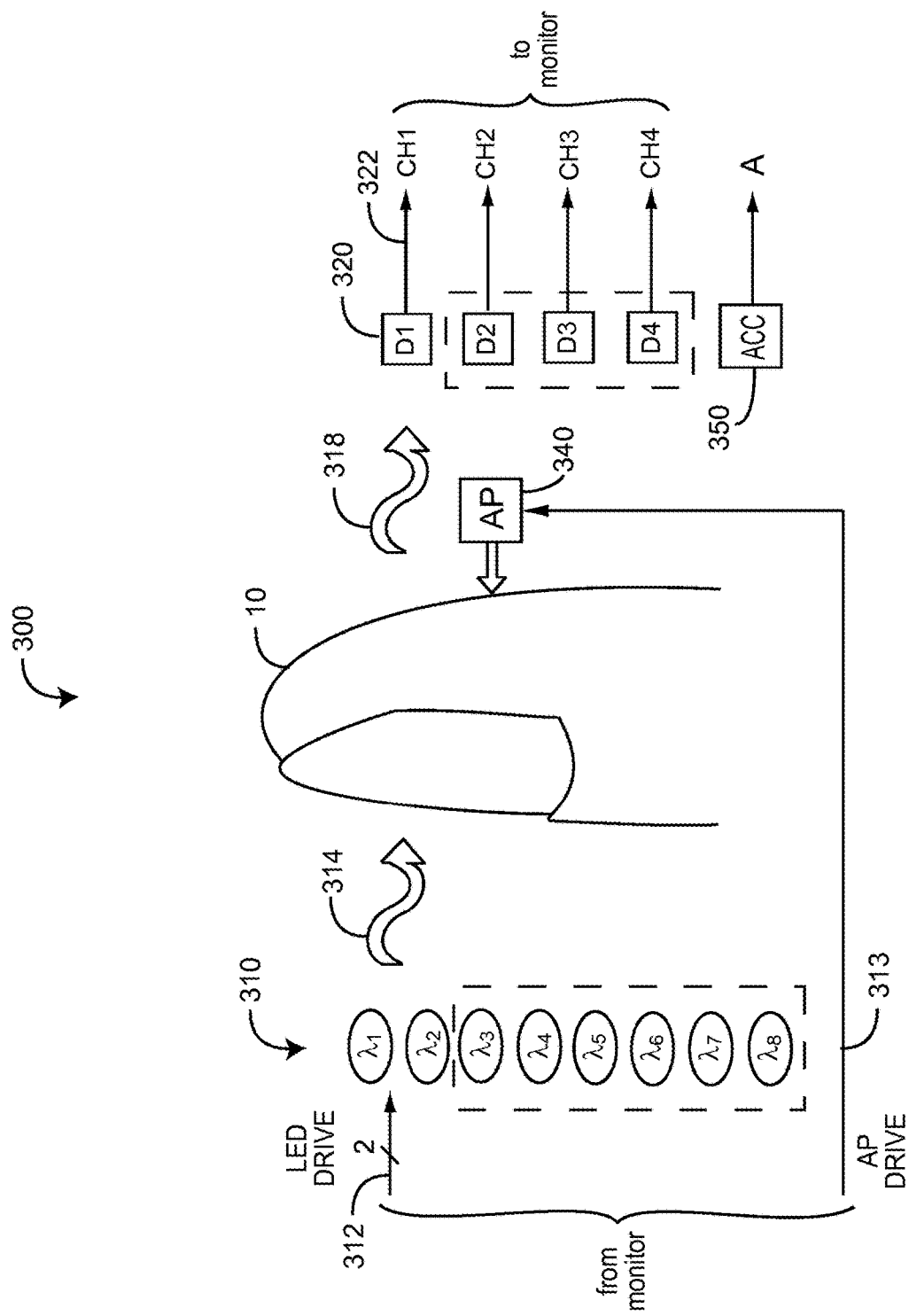
FIG. 3 is an illustration of an active-pulse blood analysis sensor that allows concurrent arterial-pulse and active-pulse blood analysis.

FIG. 3 illustrates an active-pulse blood analysis sensor 300 that allows concurrent natural pulse and active-pulse blood analysis. The sensor 300 has two or more LEDs (emitters) 310, one or more detectors 320 and an active-pulser 340. In other embodiments, the sensor 300 also has temperature sensors (not shown) responsive to the LEDs 310, the detector(s) 320 and the fingertip as well as an accelerometer 350 responsive to fingertip position and movement. The LEDs 310 are individually activated by LED drives 312 so as illuminate a tissue site 10 with optical radiation 314. The detector(s) 320 receive attenuated optical radiation 318 after absorption, reflection and diffusion by the tissue site 10 and by pulsatile blood flow within the tissue site 10. The active-pulse 340 has a motor that controls a mechanical pulser in response to an active-pulse drive signal 313. The motor has a "motor-on" state for starting the active-pulse and a "motor-off" state for stopping the active-pulse. Accordingly, the pulsatile blood flow may be heart-pulsed arterial blood flow or actively-pulsed venous and capillary blood flow, or both. The detector(s) 320 generates one or more channels 322 of plethysmograph and active-pulse signals to a DSP (not shown) within the blood analysis monitor 120 (FIG. 1) for signal processing and analysis, as described in detail below.

Figure 4:
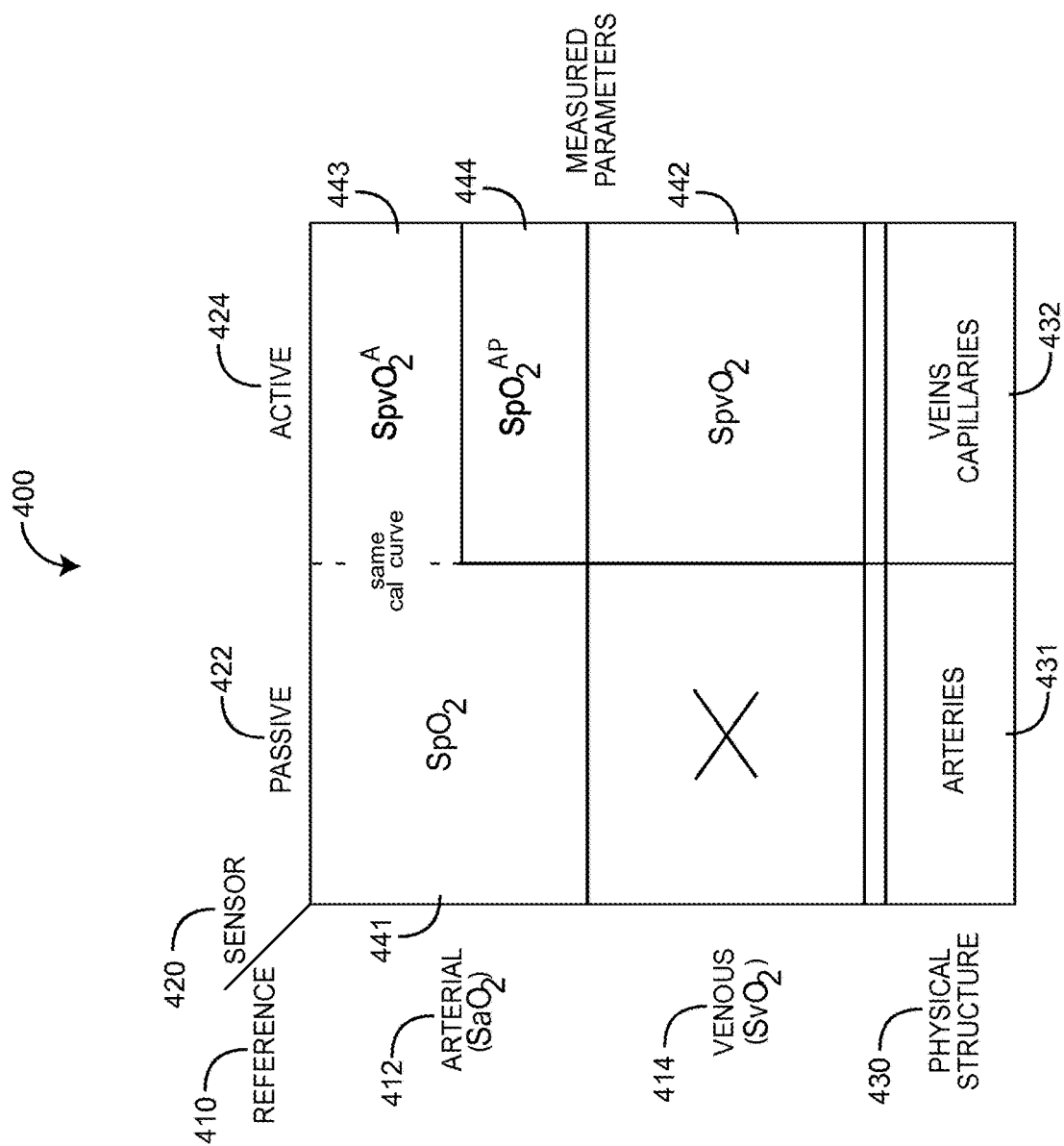
FIG. 4 is a relational chart for various active-pulse blood analysis parameters.
Figure 6:
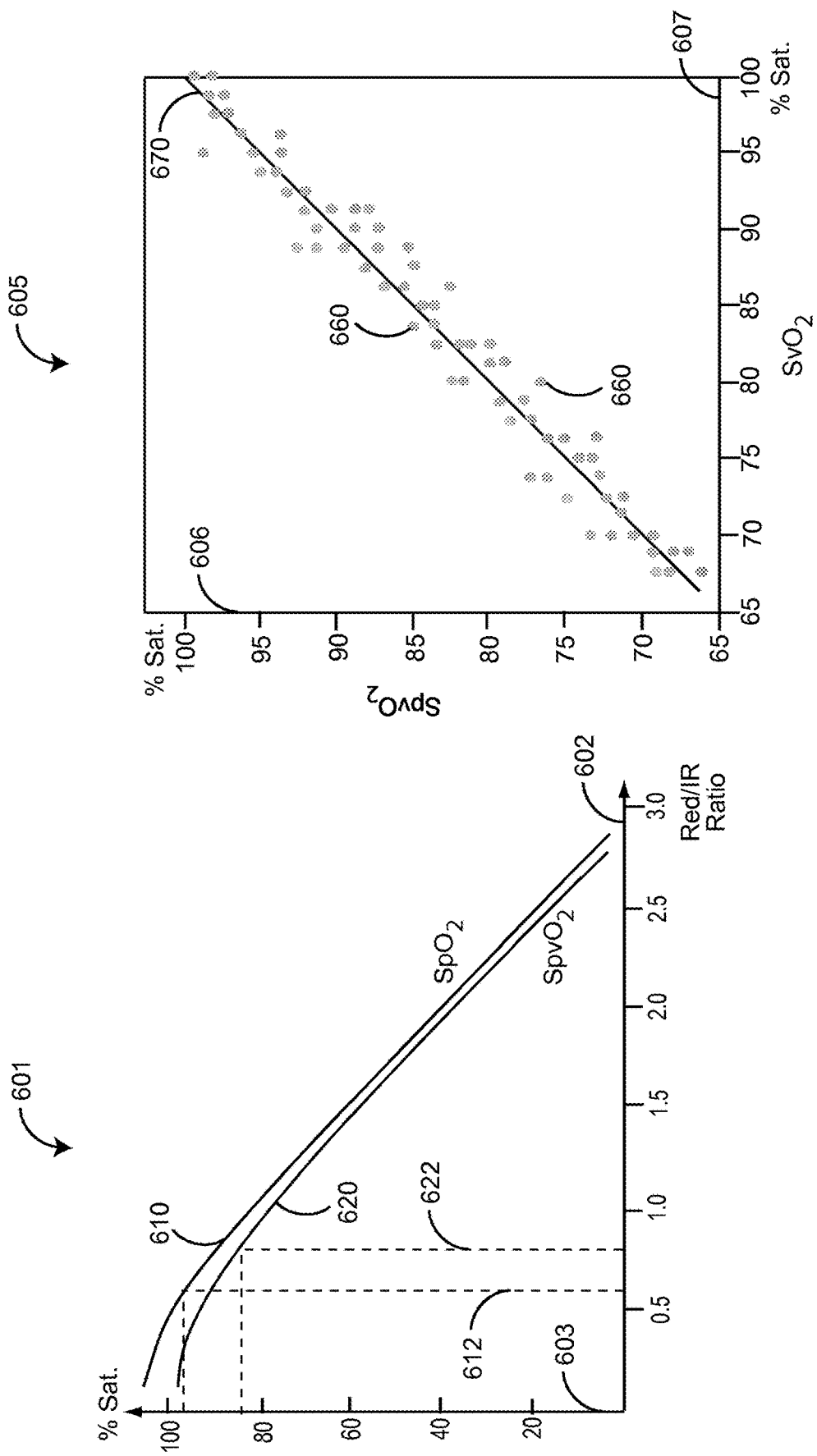
FIGS. 6A-B are graphs of active-pulse blood analysis calibration curves (cal curves)

FIG. 4 is a relational chart 400 for various active-pulse blood analysis parameters. The matrix rows 410 are invasive (blood draw) references. The matrix columns 420 are non-invasive sensor measurements. Each matrix cell 441-444 represents a blood parameter derived from an underlying calibration curve that correlates the invasive references 410 with the sensor measurements 420. FIGS. 6, 8 and 10, below, illustrate calibration curves corresponding to the cells 441-444. A "physical structure" row 430 appended at the bottom of the matrix 400 is a simple reminder that a passive sensor 422 "probes" the arteries 431, i.e. is responsive to heart-pulsed arterial blood flow, and that an active sensor 424 "probes" the capillaries and veins 432, i.e. is responsive to active-pulse induced venous blood flow. This calibration matrix 400 succinctly illustrates advantageously defined blood parameters listed within the cells 441-444, which are concurrently measured from a fingertip tissue site utilizing an active-pulse sensor 300 (FIG. 3).

As shown in FIG. 4, an SpaO$_2$ (or simply SpO$_2$) peripheral arterial oxygen saturation parameter 441 is a passive measurement 422 responsive to pulsatile arterial blood flow 431. An underlying SpO$_2$ calibration curve ("cal curve") is generated from arterial blood draws 412 correlated with the sensor-derived measurements, as described with respect to FIG. 6A, below.

Also shown in FIG. 4, an SpvO$_2$ peripheral venous oxygen saturation parameter 442 is an active-pulse measurement 424, responsive to artificially-pulsed venous and capillary blood flow 432. An underlying SpvO$_2$ cal curve is generated from venous blood draws 414 correlated with the sensor-derived measurements, as described with respect to FIGS. 6A-B, below.

Further shown in FIG. 4, an SpvO$_2^A$ peripheral venous oxygen saturation parameter 443 is an active-pulse measurement 424 responsive to artificially-pulsed venous and capillary blood flow 432. Advantageously, SpvO$_2^A$ sensor measurements utilize the same arterial ("A") cal curve 441 generated by passive sensor measurements 422 correlated with arterial blood draws 412, as cited above. SpvO$_2^A$ measurements are described with respect to FIG. 8B, below.

Additionally shown in FIG. 4, an SpO$_2^{AP}$ peripheral arterial oxygen saturation parameter 444 is an active-pulse measurement 424 responsive to artificially-pulsed venous and capillary blood flow 432 measured with an active-pulse sensor. Advantageously, SpO$_2^{AP}$ sensor measurements 444 utilize a unique active-pulse ("AP") cal curve generated from arterial blood draws 412 correlated with active-pulse sensor measurements, as described with respect to FIGS. 10A-B, below.

Figure 5:
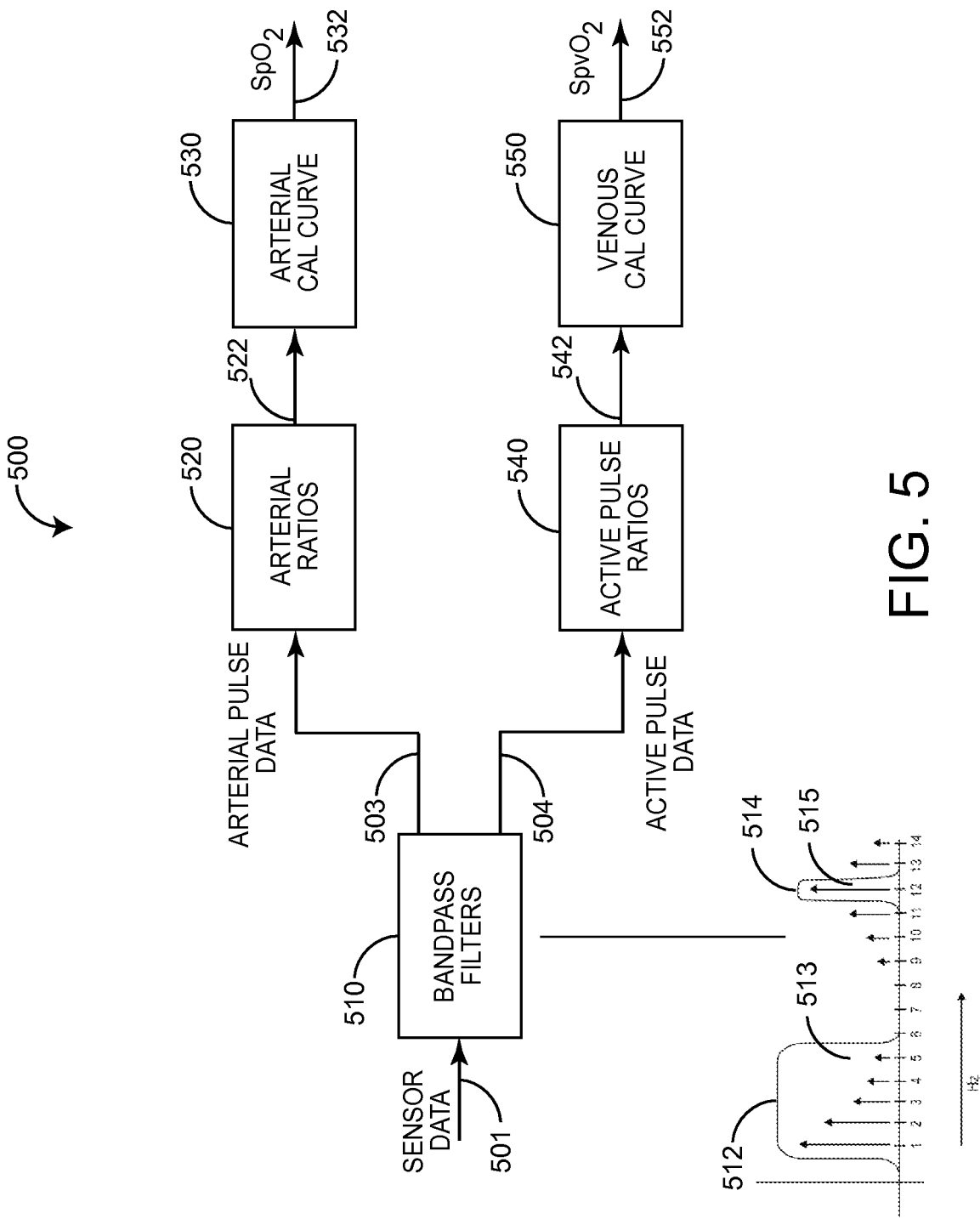
FIG. 5 is a block diagram of active-pulse blood analysis for determining $SpO_2$ using an arterial cal curve and $SpvO_2$ using a venous cal curve.

FIG. 5 illustrates an active-pulse blood analysis system 500 embodiment having a sensor data input 501, an SpO$_2$ 532 output and an SpvO2 552 output. The sensor data 501 input has arterial pulse components 513 and active-pulse components 515. Resting heart rates range around 60 bpm (1 Hz). As such, a typical arterial pulse includes a fundamental around 1 Hz and harmonics at around 2, 3, 4 and possibly 5 Hz. In an embodiment, an active-pulse is generated at around 12 Hz. As such, a typical venous-induced pulse includes a fundamental around 12 Hz and possible spurious sidebands. Accordingly, a first bandpass filter 510 has a passband 512 so as to generate arterial pulse data 503 at heart rate and heart rate harmonic frequencies 513. Also, a second bandpass filter 510 has a passband 514 so as to generate active-pulse data 504 at the known active-pulse frequency 515.

Also shown in FIG. 5, arterial ratios 520 are calculated from the arterial pulse data 503 so as to generate arterial ratio data 522. In a two wavelength sensor embodiment, arterial ratio data 522 are red/IR ratios. Multiple (more than two) wavelength ratios are described in U.S. Pat. No. 7,343,186 titled Multi-Wavelength Physiological Monitor, assigned to Cercacor and incorporated in its entirety by reference herein. Arterial ratio data 522 are input to an arterial cal curve 530 so as to generate an SpO$_2$ 532 output. Arterial cal curves are described with respect to FIG. 6A, below.

Further shown in FIG. 5, active-pulse ratios 540 are calculated from the active-pulse data 504 so as to generate active-pulse ratio data 542. In a two wavelength sensor embodiment, active-pulse ratio data 542 are red/IR ratios. Active-pulse ratio data 542 are input to a venous cal curve 550 so as to generate an SpvO$_2$ 552 output. Venous cal curves are described with respect to FIGS. 6A-B, below.

FIGS. 6A-B illustrate an active-pulse blood analysis system calibration curve (cal curve) 601 embodiment. FIG. 6A illustrates a two-dimensional SpO$_2$ (arterial) cal curve 610 and a corresponding two-dimensional SpvO$_2$ (venous) cal curve 620. The SpO$_2$ cal curve 610 is generated by comparing arterial-pulsed Red/IR plethysmograph ratios 602 derived by an optical sensor with corresponding percent oxygen saturation values 603 derived by arterial blood draws analyzed using a calibrated spectrometer. Similarly, the SpvO$_2$ cal curve 620 is generated by comparing active-pulse Red/IR plethysmograph ratios 602 with corresponding percent oxygen saturation values 603 derived by venous blood draws analyzed using the calibrated spectrometer. As examples, a Red/IR ratio of 0.6 yields a 96% arterial oxygen saturation value utilizing the arterial cal curve 610, and a Red/IR ratio of 0.8 yields a 84% venous oxygen saturation value utilizing the venous cal curve 620.

FIG. 6B illustrates a scatter plot 605 of SpvO$_2$ 606 versus SvO$_2$ 607 for an active-pulse optical sensor having greater than two-wavelengths. The scatter plot values 660 compared with a unity line 670 provide a quantitative measure of how well the underlying multi-dimensional cal curve correlates with experimental results.

Figure 7:
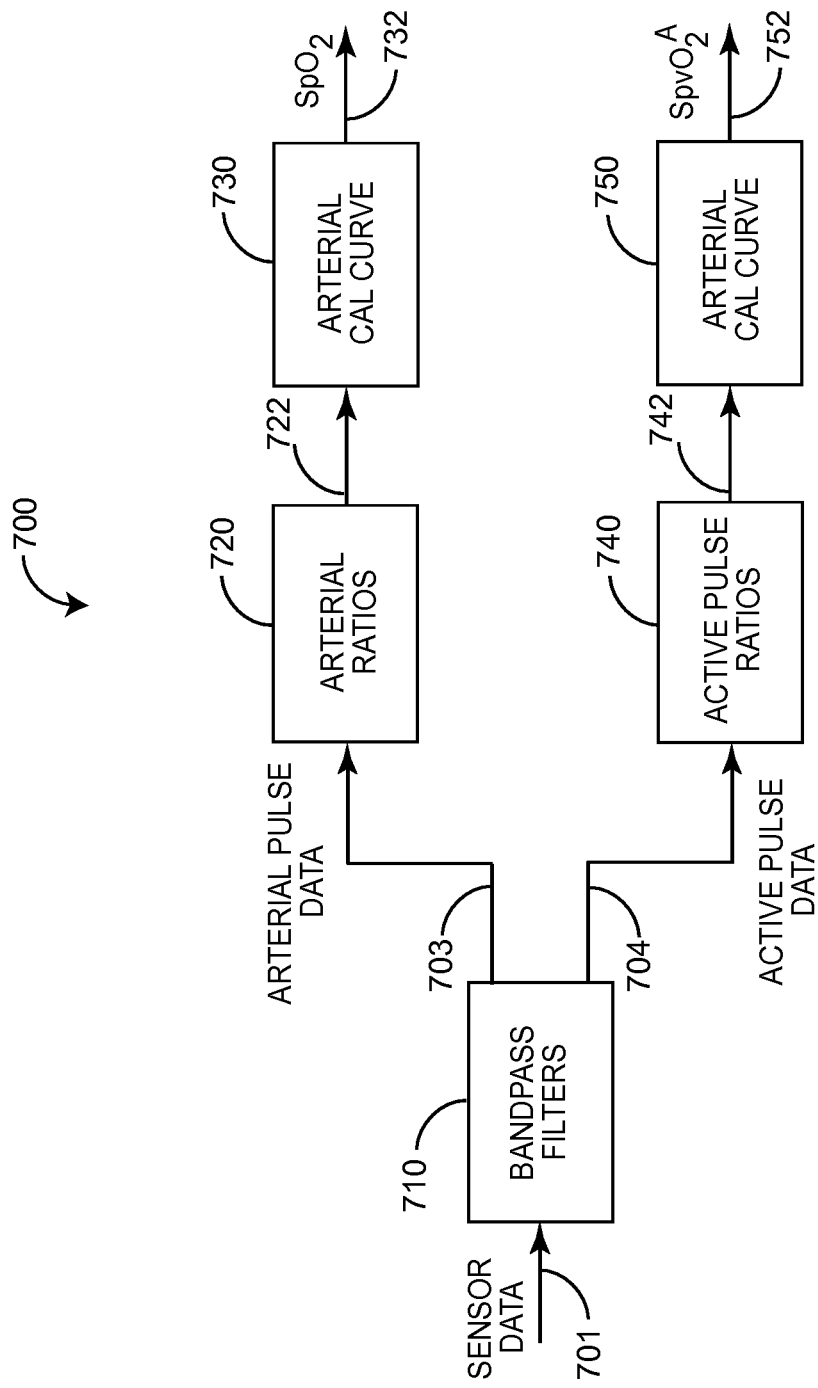
FIG. 7 is a block diagram of active-pulse blood analysis for determining $SpO_2$ and $SpvO_2^A$ using the same arterial calibration curve.

FIG. 7 illustrates an active-pulse blood analysis system 700 embodiment for advantageously determining SpO$_2$ and SpvO$_2^A$ using the same arterial calibration curve 750. The active-pulse blood analysis system 700 has a sensor data input 701, an SpO$_2$ output 732 and an SpvO$_2^A$ output 752. The bandpass filters 710 generate arterial pulse data 703 and active-pulse data 704 from the sensor data 701, as described with respect to FIG. 5, above. Arterial ratios 720 are calculated from the arterial data 703 so as to generate arterial ratio data 722, and an arterial cal curve 730 is applied to the arterial ratio data 722 so as to generate an SpO$_2$ 732 output, also described with respect to FIG. 5, above and as described in further detail with respect to FIG. 8A, below.

Further shown in FIG. 7, active-pulse ratios 740 are calculated from the active-pulse data 704 so as to generate active-pulse ratio data 742, as described with respect to FIG.

5, above. Active-pulse ratio data 742 are advantageously input to an arterial cal curve 750 so as to generate an $SpvO_2^A$ 752 output, as described in further detail with respect to FIG. 8B, below. Advantageously, the arterial cal curves 730, 750 are the same, as described in further detail with respect to FIGS. 8A-B, below. As described herein, $SpvO_2^A$ denotes a venous oxygen saturation measurement utilizing an arterial oxygen saturation cal curve, as set forth with respect to FIG. 4, above.

Figure 8B:
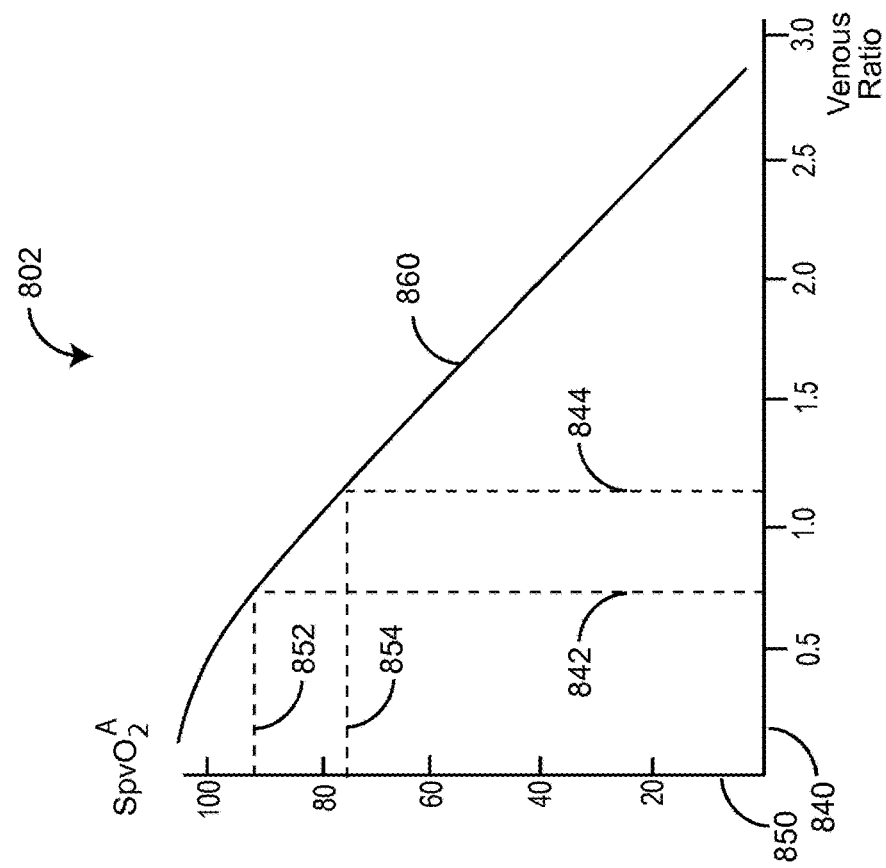
FIGS. 8A-B are graphs of active-pulse blood analysis cal curves for calculating both $SpO_2$ and $SpvO_2^A$.
Figure 8A:
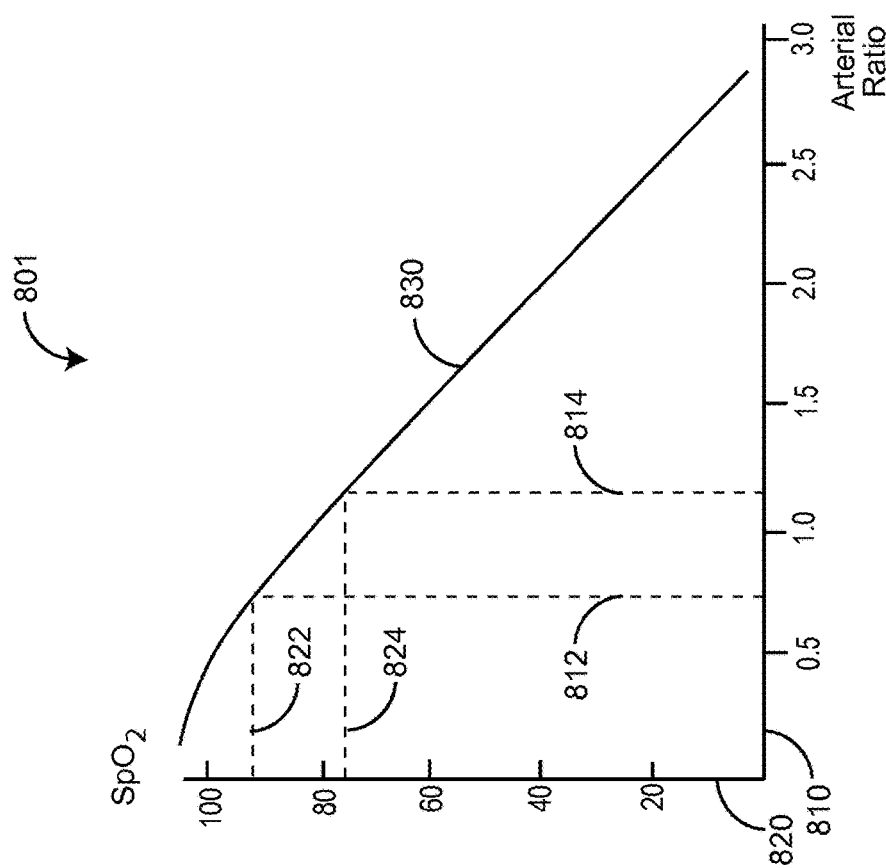

FIGS. 8A-B illustrate active-pulse blood analysis cal curves for calculating both $SpO_2$ and $SpvO_2^A$. FIG. 8A illustrates an arterial cal curve for calculating $SpO_2$. An arterial ratio graph 801 has an arterial ratio x-axis 810, an $SpO_2$ y-axis 820 and an arterial cal curve 830. The arterial cal curve 830 is numerically-derived by correlating arterial blood draws with corresponding red/IR sensor data responsive to pulsatile arterial blood flow. The cal curve 830 data is derived across a representative patient population and stored in a look-up table. A blood parameter monitor inputs sensor data, derives ratios and calculates corresponding $SpO_2$ values from the look-up table accordingly. For example, a ratio of 0.75 (812) corresponds to roughly 92% $SpO_2$ (822); and a ratio of 1.2 (814) corresponds to roughly a 76% $SpO_2$ (824).

FIG. 8B illustrates an identical arterial cal curve for calculating $SpvO_2^A$. A venous ratio graph 802 has a venous ratio x-axis 840, a $SpvO_2^A$ y-axis 850 and the same arterial cal curve 860 stored in a monitor look-up table as described with respect to FIG. 8A, above. However, the arterial cal curve 860 here is used to convert red/IR sensor data measured after attenuation by active-pulse venous blood into derived $SpvO_2^A$ values. The rationale for using an arterial cal curve for venous saturation calculations is that the optical characteristics of heart-pulse and active-pulse blood flow are the same. Hence, a ratio of 0.75 (842) corresponds to roughly 92% $SpvO_2^A$ (852); and a ratio of 1.2 (844) corresponds to roughly a 76% $SpvO_2^A$ (854).

Figure 9:
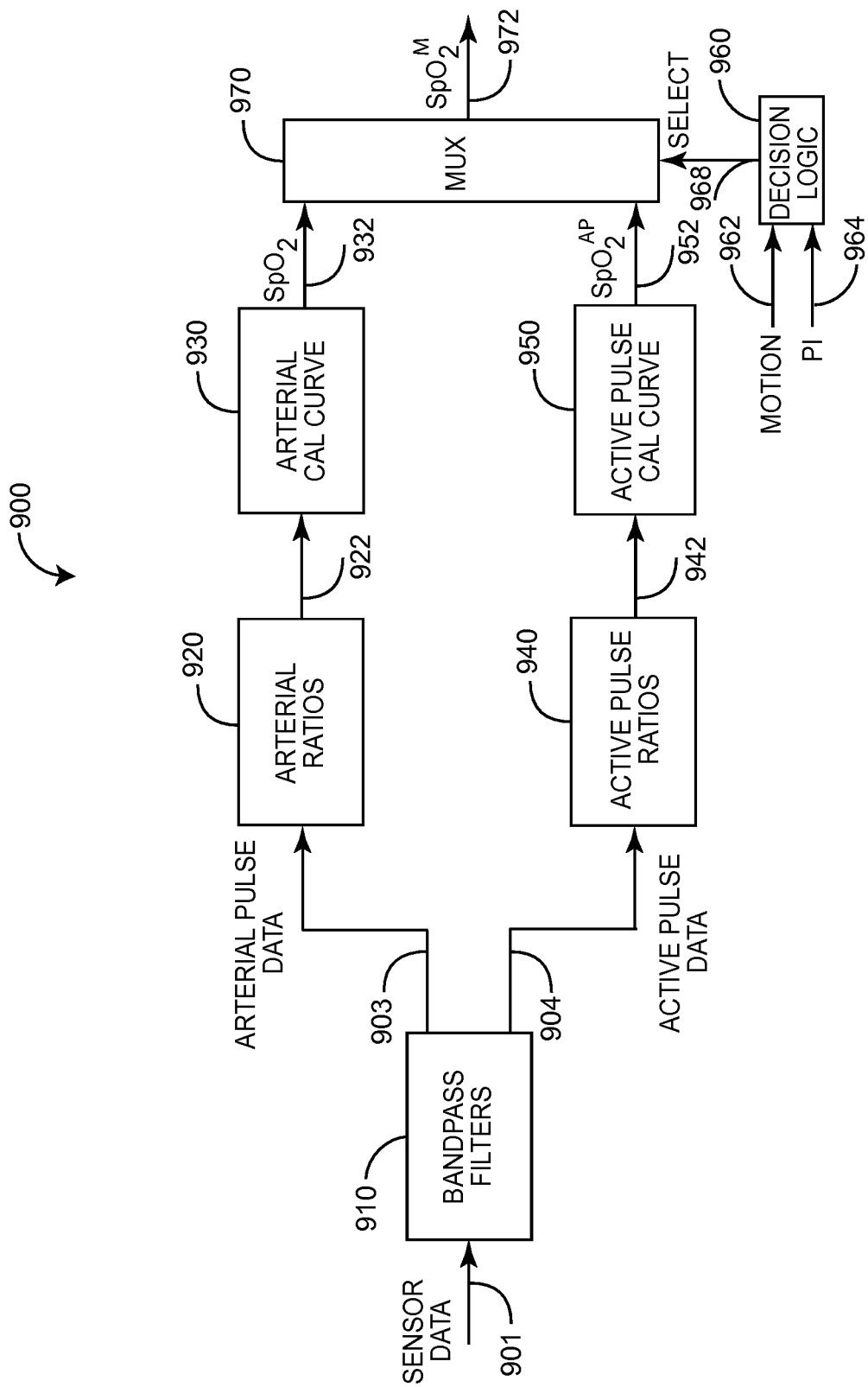
FIG. 9 is a block diagram of active-pulse blood analysis for determining $SpO_2$ and $SpO_2^{AP}$ and for combining $SpO_2$ and $SpO_2^{AP}$ based upon motion and perfusion index (PI) parameters so as to calculate a motion and low perfusion tolerant measure of arterial oxygen saturation ($SpO_2^M$)

FIG. 9 illustrates an active-pulse blood analysis system 900 embodiment for advantageously determining $SpO_2$ and $SpO_2^{AP}$ and for combining $SpO_2$ and $SpO_2^{AP}$ so as to calculate a motion tolerant measure of arterial oxygen saturation. The active-pulse blood analysis system 900 has a sensor data 901 input, an $SpO_2$ 932 output, an $SpO_2^{AP}$ 952 output, and a motion-tolerant $SpO_2^M$ oxygen saturation 972 output. The bandpass filters 910 generate arterial pulse data 903 and active-pulse data 904 from the sensor data 901, as described with respect to FIG. 5, above. Arterial ratios 920 are calculated from the arterial pulse data 903 so as to generate arterial ratio data 922, and an arterial cal curve 930 is applied to the arterial ratio data 922 so as to generate an $SpO_2$ 932 output, as described with respect to FIG. 5, above.

Further shown in FIG. 9, active-pulse ratios 940 are calculated from the active-pulse data 904 so as to generate active-pulse ratio data 942, as described with respect to FIG. 5, above. Active-pulse ratio data 942 are advantageously input to an active-pulse cal curve 950 so as to generate an $SpO_2^{AP}$ 952 output, as described in further detail with respect to FIGS. 10A-B, below.

Also shown in FIG. 9, a decision logic 960 generates a decision logic output 968. The decision logic output 968 controls a multiplexer 970 that inputs $SpO_2$ 932 and $SpO_2^{AP}$ 952 so as to generate an $SpO_2^M$ output 972 that takes into account both. In an embodiment, a motion indicator 962 an a perfusion indicator 964 are input to the decision logic 960 so that the multiplexer 970 outputs $SpO_2^{AP}$ 952 when a threshold amount of motion 962 and/or perfusion 964 is surpassed and so as to output $SpO_2$ 932 otherwise. See FIG. 11, below. In this manner, arterial oxygen saturation is advantageously estimated from active-pulse blood flow so as to negate the effect of motion-induced venous blood flow and/or low perfusion. An optical sensor accelerometer for motion detection as well as finger position sensing is described in U.S. patent application Ser. No. 13/646,659 titled Noninvasive Blood Analysis System, cited above.

Figures 10A, 10B:
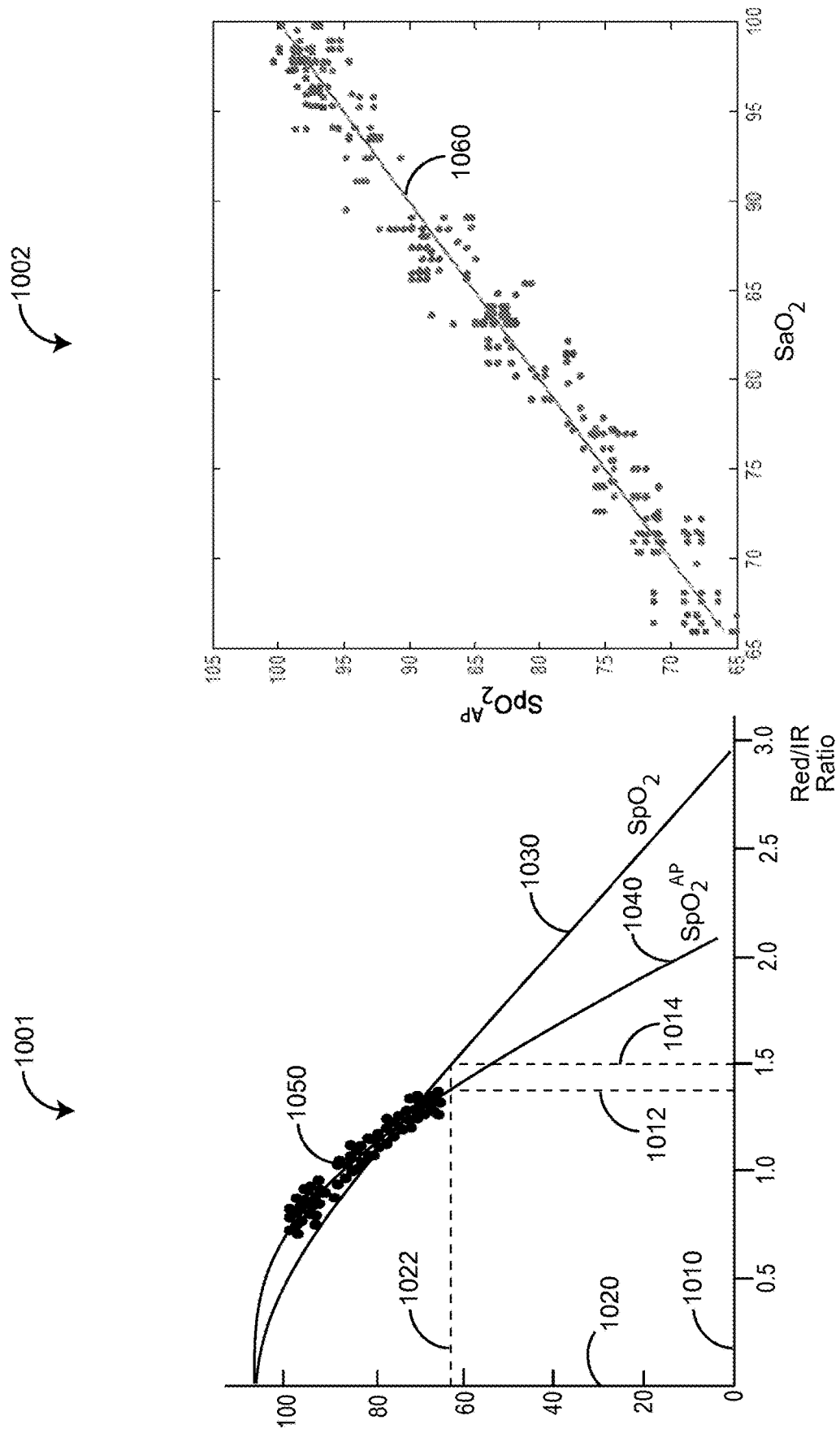
FIGS. 10A-B are graphs of active-pulse blood analysis cal curves for calculating $SpO_2$ and $SpO_2^{AP}$.

FIGS. 10A-B illustrates active-pulse blood analysis system cal curve 1001, 1002 embodiments. FIG. 10A illustrates a two-dimensional $SpO_2$ (arterial) cal curve 1030 and a corresponding two-dimensional $SpO_2^{AP}$ (active-pulse arterial) cal curve 1040. The $SpO_2$ cal curve 1030 is generated by comparing arterial-pulsed Red/IR plethysmograph ratios 1010 derived by an optical sensor with corresponding percent oxygen saturation values 1020 derived by arterial blood draws analyzed using a calibrated spectrometer, as described with respect to FIG. 6A, above. The $SpO_2^{AP}$ cal curve 1040 is generated by comparing active-pulse Red/IR plethysmograph ratios 1010 with corresponding percent oxygen saturation values 1020 derived by arterial blood draws analyzed using the calibrated spectrometer. In particular, the $SpO_2^{AP}$ cal curve corresponds relatively well to the $SpO_2$ cal curve for saturations above about 65%.

FIG. 10B illustrates a scatter plot 1002 comparing non-invasively-derived $SpO_2^{AP}$ values derived with an optical sensor having greater than two-wavelengths with corresponding invasively-derived $SaO_2$ values. A unity line 1060 provides a measure of quality for the underlying multi-dimensional $SpO_2^{AP}$ cal curve.

Figure 11:
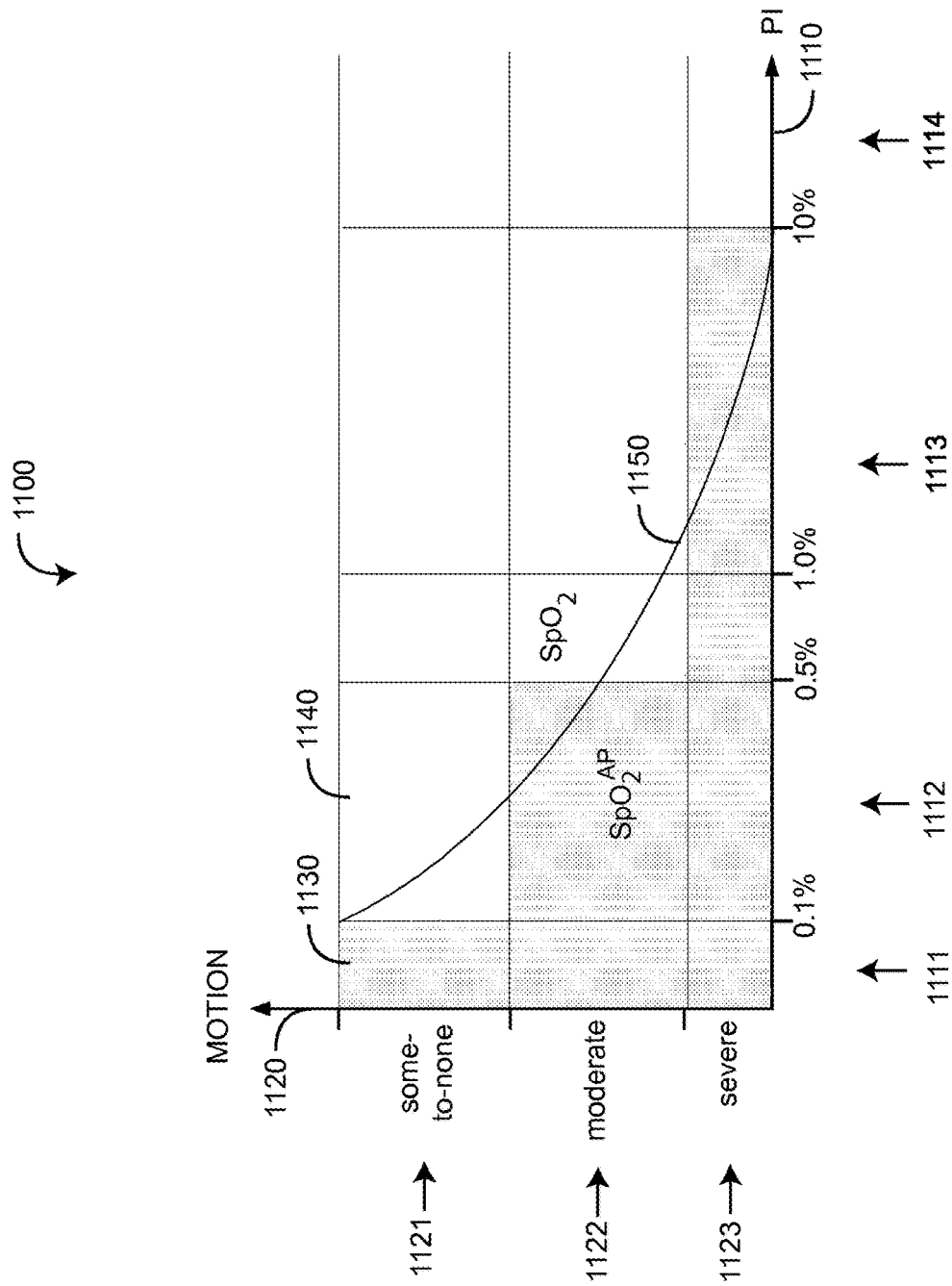
FIG. 11 is a motion versus perfusion decision graph for combining $SpO_2$ and $SpO_2^{AP}$ so as to calculate a motion and low perfusion tolerant measure of arterial oxygen saturation ($SpO_2^M$)

FIG. 11 illustrates a motion versus perfusion decision graph 1100 for combining $SpO_2$ and $SpO_2^{AP}$ so as to calculate a motion and low perfusion tolerant measure of arterial oxygen saturation $SpO_2^M$ 972 (FIG. 9). In particular, decision logic 960 (FIG. 9) determines the relative amount of motion 1120 and perfusion 1110 so as to select arterial oxygen saturation $SpO_2$ 932 (FIG. 9) or active-pulse arterial oxygen saturation $SpO_2^{AP}$ 952 (FIG. 9) as an $SpO_2^M$ output 972 (FIG. 9).

As shown in FIG. 11, in a zone embodiment, relative amounts of motion 1120 and perfusion 1110 define discrete zones that determine the use of active pulse. Generally, active pulse ($SpO_2^{AP}$) 1130 (shaded area) is used as the measure of arterial oxygen saturation ($SpO_2^M$) 972 (FIG. 9) when perfusion is relatively low and/or motion is relatively high. Arterial pulse ($SpO_2$) 1140 (unshaded area) is used as the measure of arterial oxygen saturation ($SpO_2^M$) 972 (FIG. 9) when perfusion is relatively high and/or motion is relatively low. In a particular zone embodiment, if perfusion 1110 is less than 0.1% 1111, then active pulse 1130 is used regardless of motion 1120. If perfusion 1110 is between 0.1% and 0.5% 1112, then active pulse 1130 is only used if motion is moderate 1122 to severe 1123. If perfusion 1110 is between 0.5% and 10% 1113, then active pulse is only used if motion is severe 1123, and if perfusion 1110 is over 10% 1114, active pulse is not used.

Further shown in FIG. 11, in a boundary embodiment, relative amounts of motion 1120 and perfusion 1110 are specified by a continuous boundary 1150 that determines the use of active pulse. In a particular boundary embodiment, if perfusion 1110 is less than 0.1% 1111, then active pulse 1130 is used regardless of motion 1120, and if perfusion 1110 is over 10% 1114, active pulse is not used. Otherwise, if the combination of increasing motion 1120 and decreasing perfusion 1110 falls below the boundary 1150, then active pulse oxygen saturation 1130 is used as the arterial oxygen saturation $SpO_2^M$ output 972 (FIG. 9), and if the combination of decreasing motion 1120 and increasing perfusion 1110 falls above the boundary 1150, then an arterial pulse oxygen saturation 1140 is used as the arterial oxygen saturation $SpO_2^M$ output 972 (FIG. 9).

Figure 12:
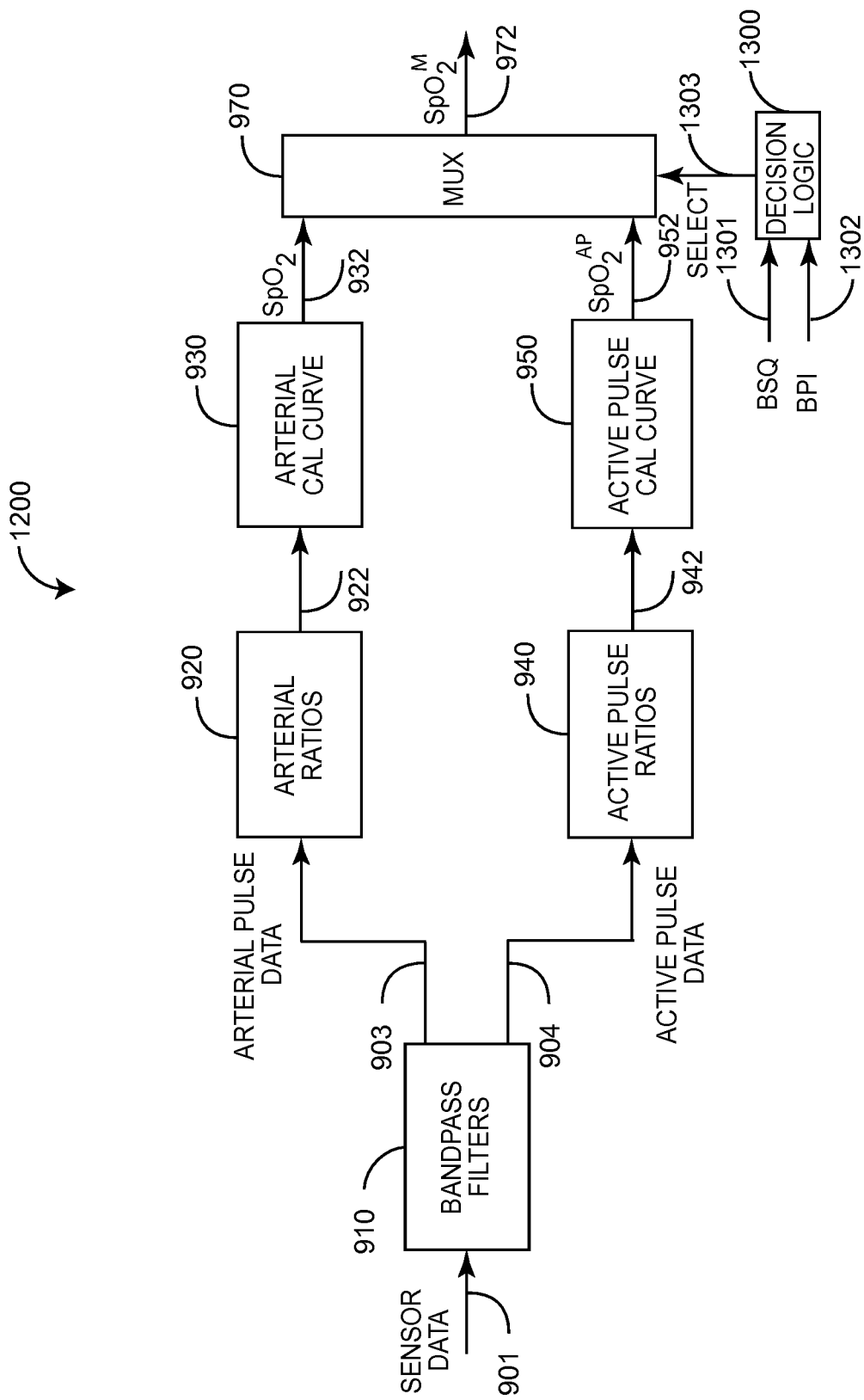
FIG. 12 is a block diagram of active-pulse blood analysis for determining $SpO_2$ and $SpO_2^{AP}$ and for combining $SpO_2$ and $SpO_2^{AP}$ based upon BSQ (Boolean signal quality) and BPI (Boolean perfusion index) parameters so as to calculate a motion and low perfusion tolerant measure of arterial oxygen saturation ($SpO_2^M$)

FIG. 12 illustrates another active-pulse blood analysis embodiment for determining $SpO_2$ and $SpO_2^{AP}$ and for combining $SpO_2$ and $SpO_2^{AP}$ based upon BSQ (Boolean signal quality) and BPI (Boolean perfusion index) parameters so as to calculate a motion and low perfusion tolerant measure of arterial oxygen saturation $SpO_2^M$ (multiplexed oxygen saturation). In particular, FIG. 12 differs from FIG. 9, above, in that the multiplexer ("mux") select 1303 input is based upon Boolean decision logic 1300 responsive to BWQ 1301 and BPI 1302 inputs.

As shown in FIG. 12, in an embodiment, BSQ=0 indicates low signal quality; BSQ=1 indicates high signal quality; BPI=0 indicates low perfusion; and BPI=1 indicates good perfusion. In an embodiment, BPI=0 when PI is below 1%. In an embodiment, BSQ is a direct measure of the amount of motion in the signal. In a particular embodiment, accelerometer 350 (FIG. 3) values (x, y and z axis) are compared against a threshold and BSQ=0 when a specified percentage of the samples for any one of the three axis (x, y or z) have an accelerometer output greater than the threshold. In an embodiment, the threshold is 0.3 g and the specified percentage of samples is 50%. Decision logic 1300 is described in detail with respect to FIG. 13, below.

Figure 13:
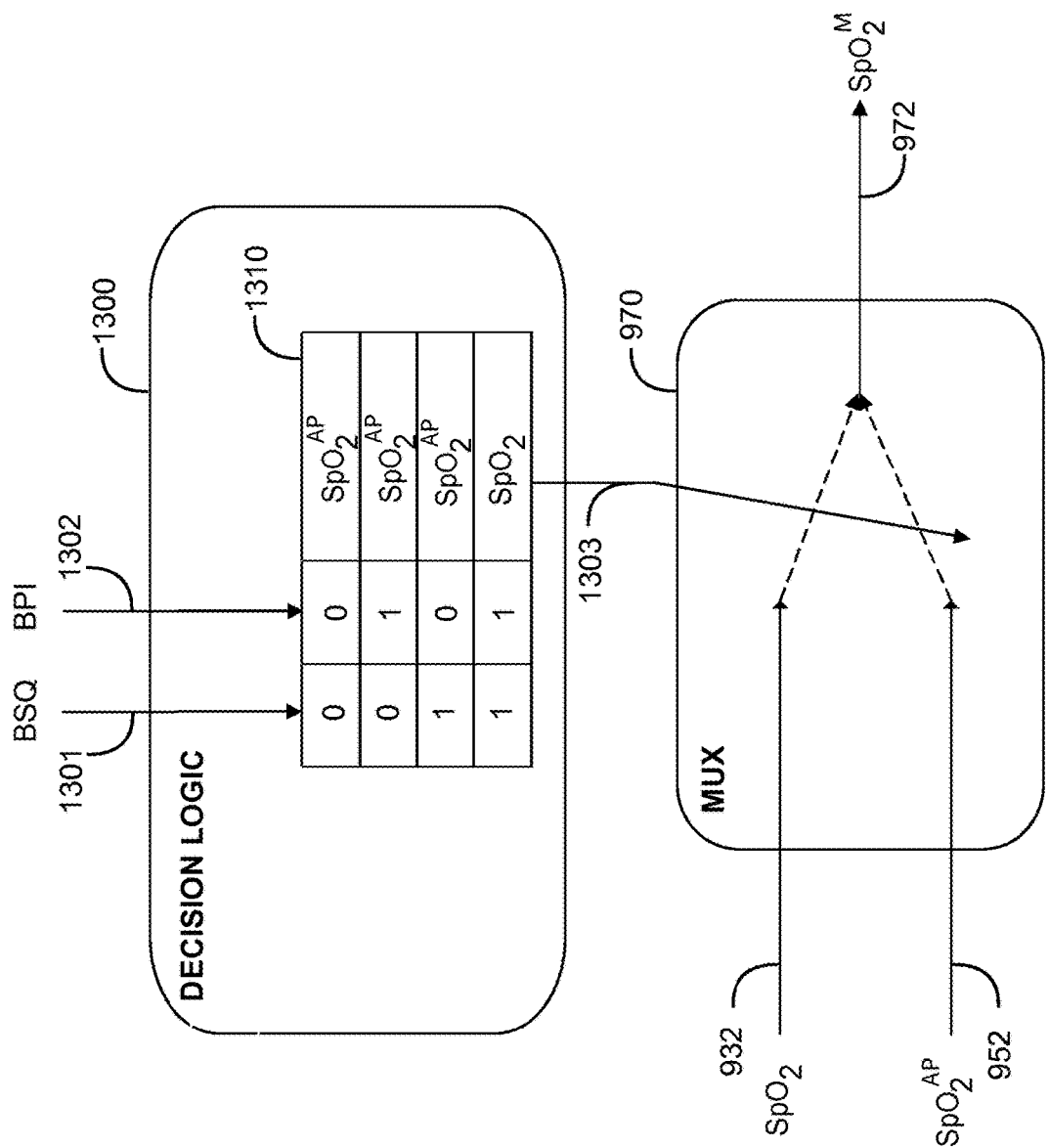
FIG. 13 is a block diagram of a decision logic embodiment for combining $SpO_2$ and $SpO_2^{AP}$ based upon BSQ and BPI so as to calculate $SpO_2^M$.

FIG. 13 illustrates a decision logic 1300 embodiment for combining $SpO_2$ 932 and $SpO_2^{AP}$ 952 inputs into a $SpO_2^M$ 972 output. Decision logic 1300 has BSQ 1301 and BPI 1302 inputs as described with respect to FIG. 12, above. $SpO_2^{AP}$ 952 is selected as the $SpO_2^M$ 972 output for all combinations of either BSQ=0 or BPI=0, i.e. if either the signal quality or the PI is low. $SpO_2$ 932 is selected as the $SpO_2^M$ 972 output only if BSQ=1 and BPI=1, i.e. if both the signal quality and the PI is high.

An active-pulse blood analysis system has been disclosed in detail in connection with various embodiments. These embodiments are disclosed by way of examples only and are not to limit the scope of the claims that follow. One of ordinary skill in art will appreciate many variations and modifications.

What is claimed is:

1. An active-pulse blood analysis system, comprising:
an optical emitter that that illuminates a tissue site with multiple wavelengths of optical radiation;
an optical sensor that outputs sensor signals responsive to the optical radiation after attenuation by pulsatile blood flow within the tissue site;
a monitor that receives the sensor signals and generates an arterial pulse ratio and an active pulse ratio according to the wavelengths;
one or more memory devices storing an arterial calibration curve that relates arterial pulse ratios to arterial oxygen saturation values (SpO2);
one or more memory devices storing an active pulse calibration curve that relates active pulse ratios to arterial oxygen saturation values (SpO2AP);
one or more processors configured to:
select a first arterial oxygen saturation value (SpO2) from the arterial calibration curve based on the arterial pulse ratio generated by the monitor, and
select a second arterial oxygen saturation value (SpO2AP) from the active pulse calibration curve based on the active pulse ratio generated by the monitor; and
a selection module that outputs a third arterial oxygen saturation value (SpO2M) selected from one of the first arterial oxygen saturation value (SpO2) and the second arterial oxygen saturation value (SpO2AP) based on a signal quality input and a perfusion index input.

2. The active-pulse blood analysis system according to claim 1, wherein the third arterial oxygen saturation (SpO2M) is tolerant to at least one of motion, low perfusion and low signal quality.

3. The active-pulse blood analysis system according to claim 1, wherein the signal quality input is a Boolean signal quality input (BSQ) and the perfusion index input is a Boolean perfusion index input (BPI).

4. The active-pulse blood analysis system according to claim 3, wherein the selection module outputs the first arterial oxygen saturation only when the BSQ and the BPI are both equal to 1.

5. An active-pulse blood analysis method comprising:
inputting optical sensor data;
calculating arterial pulse ratios from the optical sensor data;
calculating active pulse ratios from the optical sensor data;
applying an arterial calibration curve stored in one or more memory devices to the arterial pulse ratios so as to generate an SpO2 parameter indicative of arterial oxygen saturation determined from an arterial pulse;
applying an active pulse calibration curve stored in one or more memory devices to the arterial pulse ratios so as to generate an SpO2AP parameter indicative of arterial oxygen saturation determined from an active pulse; and
choosing between the SpO2 parameter and the SpO2AP parameter so as to generate an SpO2M output parameter, the SpO2M output parameter comprising either the SpO2 parameter or the SpO2AP parameter, based on signal quality input.

6. The active-pulse blood analysis method according to claim 5, wherein the SpO2M output parameter is indicative of an arterial oxygen saturation measurement tolerant to at least one of motion, low perfusion and low signal quality.

7. The active-pulse blood analysis method according to claim 5, wherein choosing the signal quality input comprises a Boolean signal quality (BSI) and a Boolean perfusion index input (BPI).

8. The active-pulse blood analysis method according to claim 7, further comprising measuring a perfusion index (PI), and wherein the Boolean perfusion input (BPI) is zero when the perfusion index (PI) is below a first threshold boundary.

9. The active-pulse blood analysis method according to claim 8, further comprising measuring an acceleration of an optical sensor, and wherein the Boolean signal quality (BSQ) is zero when the measured acceleration is above a second threshold boundary.

10. The active-pulse blood analysis method according to claim 9, wherein the second threshold boundary is an acceleration of 0.3 g.

11. The active-pulse blood analysis method according to claim 8, wherein the first threshold boundary is a perfusion index (PI) of 1%.

12. An active-pulse blood analysis apparatus comprising:
an optical emitter means for transmitting multiple wavelengths of light into a tissue site;
an optical sensor means for detecting the transmitted light after attenuation by arterial blood flow and active pulsed blood flow within the tissue site so as to generate plethysmograph data;
a processor means for calculating an arterial pulse ratio from the plethysmograph data and an active pulse ratio from the plethysmograph data;

a means for storing:

an arterial calibration curve means for relating arterial pulse ratios to oxygen saturation values (SpO2); and an active pulse calibration curve means for relating active pulse ratios to active pulse oxygen saturation values (SpO2AP);

a means for selecting:

an oxygen saturation value (SpO2) from the arterial calibration curve means based on the arterial pulse ratio; and an active pulse oxygen saturation value (SpO2AP) from the active pulse calibration curve means based on the active pulse ratio; and a means for selecting either the oxygen saturation value (SpO2) or the active pulse oxygen saturation value (SpO2AP) as an oxygen saturation value (SpO2M) based on a signal quality input and a perfusion index input.

13. The active-pulse blood analysis apparatus according to claim 12, wherein the signal quality input is a Boolean signal quality (BSQ) and the perfusion index input is a Boolean perfusion index (BPI).

14. The active-pulse blood analysis apparatus of claim 13, wherein the Boolean perfusion input (BPI) is zero when a measured perfusion index (PI) is below a first threshold boundary.

15. The active-pulse blood analysis apparatus according to claim 14, wherein the first threshold boundary is a perfusion index (PI) of 1%.

16. The active-pulse blood analysis apparatus of claim 13, wherein the Boolean signal quality input (BPI) is zero when a measured acceleration of the optical sensor is greater than a second threshold boundary.

17. The active-pulse blood analysis apparatus according to claim 16, wherein the second threshold boundary is an acceleration of 0.3 g.

* * * * *

UNITED STATES PATENT AND TRADEMARK OFFICE
CERTIFICATE OF CORRECTION

PATENT NO. : 11,839,470 B2
APPLICATION NO. : 17/576281
DATED : December 12, 2023
INVENTOR(S) : Kiani et al.

It is certified that error appears in the above-identified patent and that said Letters Patent is hereby corrected as shown below:

On the Title Page

Page 3, Column 2 (U.S. Patent Documents), Line 45, delete "Al Ali" and insert -- Al-Ali --.

Page 5, Column 2 (U.S. Patent Documents), Line 58, delete "Al Ali" and insert -- Al-Ali --.

In the Specification

Column 1, Line 2, below "SYSTEM" insert -- PRIORITY CLAIM AND REFERENCE TO RELATED APPLICATIONS --.

Column 1, Line 21-22, below "herein." delete "PRIORITY CLAIM AND REFERENCE TO RELATED APPLICATIONS".

Column 1, Line 24-35 (approx.), below "APPLICATIONS" delete "The present application is a continuation-in-part of U.S. patent application Ser. No. 14/153,393, filed Jan. 13, 2014, titled Active-Pulse Blood Analysis System, which claims priority benefit under 35 U.S.C. § 119(e) to U.S. Provisional Patent Application Ser. No. 61/752,976, filed Jan. 16, 2013, titled Active-Pulse Blood Analysis System; the present application claims priority benefit under 35 U.S.C. § 119(e) to U.S. Provisional Patent Application Ser. No. 61/844,699, filed Jul. 10, 2013, titled Active-Pulse Blood Analysis System; the above-referenced patent application and provisional patent applications are hereby incorporated in their entireties by reference herein.".

Column 7, Line 64, delete "SpvO2" and insert -- $SpvO_2$ --.

Column 9, Line 63, delete "an" and insert -- and --.

In the Claims

Column 11, Line 44, Claim 1, delete "that that" and insert -- that --.

Signed and Sealed this
Fifth Day of March, 2024

Katherine Kelly Vidal
*Director of the United States Patent and Trademark Office*

CERTIFICATE OF CORRECTION (continued)
U.S. Pat. No. 11,839,470 B2

Column 11, Line 54, Claim 1, delete "(SpO2);" and insert -- (SpO$_2$); --.

Column 11, Line 57, Claim 1, delete "(SpO2AP);" and insert -- (SpO$_2^{AP}$); --.

Column 11, Line 59, Claim 1, delete "(SpO2)" and insert -- (SpO$_2$) --.

Column 11, Line 62, Claim 1, delete "(SpO2AP)" and insert -- (SpO$_2^{AP}$) --.

Column 11, Line 66, Claim 1, delete "(SpO2M)" and insert -- (SpO$_2^{M}$) --.

Column 11, Line 67, Claim 1, delete "(SpO2)" and insert -- (SpO$_2$) --.

Column 12, Line 1, Claim 1, delete "(SpO2AP)" and insert -- (SpO$_2^{AP}$) --.

Column 12, Line 5, Claim 2, delete "(SpO2M)" and insert -- (SpO$_2^{M}$) --.

Column 12, Line 23, Claim 5, delete "SpO2" and insert -- SpO$_2$ --.

Column 12, Line 27, Claim 5, delete "SpO2AP" and insert -- SpO$_2^{AP}$ --.

Column 12, Line 29, Claim 5, delete "SpO2" and insert -- SpO$_2$ --.

Column 12, Line 29, Claim 5, delete "SpO2AP" and insert -- SpO$_2^{AP}$ --.

Column 12, Line 30, Claim 5, delete "SpO2M" and insert -- SpO$_2^{M}$ --.

Column 12, Line 31, Claim 5, delete "SpO2M" and insert -- SpO$_2^{M}$ --.

Column 12, Line 32, Claim 5, delete "SpO2" and insert -- SpO$_2$ --.

Column 12, Line 32, Claim 5, delete "SpO2AP" and insert -- SpO$_2^{AP}$ --.

Column 12, Line 35, Claim 6, delete "SpO2M" and insert -- SpO$_2^{M}$ --.

Column 13, Line 3, Claim 12, delete "(SpO2);" and insert -- (SpO$_2$); --.

Column 13, Line 6, Claim 12, delete "(SpO2AP);" and insert -- (SpO$_2^{AP}$); --.

Column 13, Line 8, Claim 12, delete "(SpO2)" and insert -- (SpO$_2$) --.

Column 13, Line 11, Claim 12, delete "(SpO2AP)" and insert -- (SpO$_2^{AP}$) --.

Column 13, Line 16, Claim 12, delete "(SpO2)" and insert -- (SpO$_2$) --.

CERTIFICATE OF CORRECTION (continued)
U.S. Pat. No. 11,839,470 B2

Column 13, Line 17, Claim 12, delete "(SpO2AP)" and insert -- ($SpO_2^{AP}$) --.

Column 13, Line 17, Claim 12, delete "(SpO2M)" and insert -- ($SpO_2^{M}$) --.